United States Patent
Nau, Jr. et al.

(10) Patent No.: US 9,833,285 B2
(45) Date of Patent: Dec. 5, 2017

(54) OPTICAL SEALING DEVICE WITH CUTTING ABILITY

(71) Applicant: COVIDIEN LP, Mansfield, MA (US)

(72) Inventors: William H. Nau, Jr., Longmont, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 921 days.

(21) Appl. No.: 13/920,643

(22) Filed: Jun. 18, 2013

(65) Prior Publication Data

US 2014/0025053 A1    Jan. 23, 2014

Related U.S. Application Data

(60) Provisional application No. 61/672,350, filed on Jul. 17, 2012.

(51) Int. Cl.
*A61B 18/18* (2006.01)
*A61B 18/20* (2006.01)
(Continued)

(52) U.S. Cl.
CPC .............. *A61B 18/18* (2013.01); *A61B 18/20* (2013.01); *A61B 2017/2926* (2013.01);
(Continued)

(58) Field of Classification Search
CPC ............ A61B 18/20; A61B 2017/2926; A61B 2018/00601; A61B 17/2909; A61B 2018/0063; A61B 2018/00958
See application file for complete search history.

(56) References Cited

U.S. PATENT DOCUMENTS

D249,549 S    9/1978  Pike
4,126,136 A   11/1978  Auth et al.
(Continued)

FOREIGN PATENT DOCUMENTS

| CN | 201299462 | 9/2009 |
|---|---|---|
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |

(Continued)

OTHER PUBLICATIONS

U.S. Appl. No. 08/926,869, filed Sep. 10, 1997, James G. Chandler.
(Continued)

*Primary Examiner* — Timothy J Neal

(57) ABSTRACT

A forceps includes an end effector assembly, a handle assembly, a first switch assembly, and a second switch assembly. The end effector includes first and second jaw members, at least one of the jaw members movable relative to the other between a spaced-apart position, a first approximated position and a second approximated position, at least one of the jaw members adapted to connect to a source of energy. The handle assembly includes a movable handle operably coupled to the end effector, and is movable between an initial stage, a first actuated stage, and a second actuated stage. The first switch assembly is activatable to supply a first energy to the end effector to seal tissue grasped, and the second switch assembly is activatable to supply a second energy to the end effector to cut tissue grasped.

6 Claims, 8 Drawing Sheets

(51) Int. Cl.
    *A61B 17/29* (2006.01)
    *A61B 18/00* (2006.01)
(52) U.S. Cl.
    CPC ........... *A61B 2018/0063* (2013.01); *A61B 2018/00601* (2013.01); *A61B 2018/00958* (2013.01)

(56) References Cited

U.S. PATENT DOCUMENTS

| | | | |
|---|---|---|---|
| 4,266,547 A | 5/1981 | Komiya |
| D263,020 S | 2/1982 | Rau, III |
| D295,893 S | 5/1988 | Sharkany et al. |
| D295,894 S | 5/1988 | Sharkany et al. |
| 4,757,425 A | 7/1988 | Waltz |
| D298,353 S | 11/1988 | Manno |
| D299,413 S | 1/1989 | DeCarolis |
| 4,854,320 A | 8/1989 | Dew et al. |
| 5,037,433 A | 8/1991 | Wilk et al. |
| 5,055,983 A | 10/1991 | Hunold et al. |
| 5,071,417 A | 12/1991 | Sinofsky |
| 5,147,356 A | 9/1992 | Bhatta |
| 5,169,396 A | 12/1992 | Dowlatshahi et al. |
| 5,209,748 A | 5/1993 | Daikuzono |
| 5,217,460 A | 6/1993 | Knoepfler |
| 5,258,006 A | 11/1993 | Rydell et al. |
| D343,453 S | 1/1994 | Noda |
| 5,318,589 A | 6/1994 | Lichtman |
| D348,930 S | 7/1994 | Olson |
| D349,341 S | 8/1994 | Lichtman et al. |
| 5,334,191 A | 8/1994 | Poppas et al. |
| 5,336,220 A | 8/1994 | Ryan et al. |
| 5,336,221 A | 8/1994 | Anderson |
| 5,342,358 A | 8/1994 | Daikuzono |
| 5,344,418 A | 9/1994 | Ghaffari |
| 5,376,094 A | 12/1994 | Kline |
| D354,564 S | 1/1995 | Medema |
| 5,383,880 A | 1/1995 | Hooven |
| 5,409,481 A | 4/1995 | Poppas et al. |
| D358,887 S | 5/1995 | Feinberg |
| 5,415,657 A | 5/1995 | Taymor-Luria |
| 5,470,331 A | 11/1995 | Daikuzono |
| 5,569,241 A | 10/1996 | Edwards |
| D384,413 S | 9/1997 | Zlock et al. |
| 5,662,643 A | 9/1997 | Kung et al. |
| 5,762,609 A | 6/1998 | Benaron et al. |
| 5,769,791 A | 6/1998 | Benaron et al. |
| H1745 H | 8/1998 | Paraschac |
| 5,807,393 A | 9/1998 | Williamson, IV et al. |
| 5,827,281 A | 10/1998 | Levin |
| 5,827,323 A | 10/1998 | Klieman et al. |
| D402,028 S | 12/1998 | Grimm et al. |
| 5,849,022 A | 12/1998 | Sakashita et al. |
| D408,018 S | 4/1999 | McNaughton |
| 5,921,916 A | 7/1999 | Aeikens et al. |
| 5,957,937 A | 9/1999 | Yoon |
| D416,089 S | 11/1999 | Barton et al. |
| 5,993,466 A | 11/1999 | Yoon |
| 5,993,467 A | 11/1999 | Yoon |
| 6,004,332 A | 12/1999 | Yoon et al. |
| 6,024,741 A | 2/2000 | Williamson, IV et al. |
| RE36,634 E | 3/2000 | Ghaffari |
| 6,039,729 A | 3/2000 | Durville |
| 6,053,909 A | 4/2000 | Shadduck |
| 6,053,933 A | 4/2000 | Balazs et al. |
| D424,694 S | 5/2000 | Tetzlaff et al. |
| D425,201 S | 5/2000 | Tetzlaff et al. |
| 6,063,085 A | 5/2000 | Tay et al. |
| 6,086,586 A | 7/2000 | Hooven |
| 6,086,601 A | 7/2000 | Yoon |
| H1904 H | 10/2000 | Yates et al. |
| 6,126,665 A | 10/2000 | Yoon |
| 6,143,005 A | 11/2000 | Yoon et al. |
| 6,208,466 B1 | 3/2001 | Liu et al. |
| 6,221,069 B1 | 4/2001 | Daikuzono |
| 6,224,614 B1 | 5/2001 | Yoon |
| 6,248,117 B1 | 6/2001 | Blatter |
| 6,270,497 B1 | 8/2001 | Sekino et al. |
| 6,283,961 B1 | 9/2001 | Underwood et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,508,816 B2 | 1/2003 | Shadduck |
| 6,569,173 B1 | 5/2003 | Blatter et al. |
| 6,623,494 B1 | 9/2003 | Blatter |
| 6,626,901 B1 | 9/2003 | Treat et al. |
| 6,663,639 B1 | 12/2003 | Laufer et al. |
| 6,689,131 B2 | 2/2004 | McClurken |
| 6,726,694 B2 | 4/2004 | Blatter et al. |
| 6,743,239 B1 | 6/2004 | Kuehn et al. |
| 6,766,187 B1 | 7/2004 | Black et al. |
| D493,888 S | 8/2004 | Reschke |
| 6,773,409 B2 | 8/2004 | Truckai et al. |
| 6,773,441 B1 | 8/2004 | Laufer et al. |
| 6,786,905 B2 | 9/2004 | Swanson et al. |
| D496,997 S | 10/2004 | Dycus et al. |
| D499,181 S | 11/2004 | Dycus et al. |
| D502,994 S | 3/2005 | Blake, III |
| 6,860,880 B2 | 3/2005 | Treat et al. |
| 6,908,463 B2 | 6/2005 | Treat et al. |
| 6,932,816 B2 | 8/2005 | Phan |
| D509,297 S | 9/2005 | Wells |
| 7,025,765 B2 | 4/2006 | Balbierz et al. |
| 7,052,489 B2 | 5/2006 | Griego et al. |
| D525,361 S | 7/2006 | Hushka |
| 7,083,618 B2 * | 8/2006 | Couture ............ A61B 18/1445 606/49 |
| D531,311 S | 10/2006 | Guerra et al. |
| 7,115,139 B2 | 10/2006 | McClurken et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| 7,169,146 B2 | 1/2007 | Truckai et al. |
| 7,179,255 B2 | 2/2007 | Lettice et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,318,823 B2 | 1/2008 | Sharps et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,414,724 B2 | 8/2008 | Eckert et al. |
| 7,452,355 B2 | 11/2008 | Khomchenko |
| D582,038 S | 12/2008 | Swoyer et al. |
| 7,588,565 B2 | 9/2009 | Marchitto et al. |
| 7,655,007 B2 | 2/2010 | Baily |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,908 B2 | 7/2010 | Swanson |
| D621,503 S | 8/2010 | Otten et al. |
| 7,771,374 B2 | 8/2010 | Slatkine |
| 7,775,103 B2 | 8/2010 | Veerasamy |
| D627,462 S | 11/2010 | Kingsley |
| D628,289 S | 11/2010 | Romero |
| D628,290 S | 11/2010 | Romero |
| D630,324 S | 1/2011 | Reschke |
| 7,967,839 B2 | 6/2011 | Flock et al. |
| D649,249 S | 11/2011 | Guerra |
| D649,643 S | 11/2011 | Allen, IV et al. |
| D661,394 S | 6/2012 | Romero et al. |
| 8,241,282 B2 | 8/2012 | Unger et al. |
| 8,251,891 B2 | 8/2012 | Moskowitz et al. |

(56) References Cited

U.S. PATENT DOCUMENTS

| | | | |
|---|---|---|---|
| 8,388,612 B2 | 3/2013 | Dunning et al. | |
| 8,444,636 B2 | 5/2013 | Shadduck et al. | |
| 2003/0018331 A1 | 1/2003 | Dycus et al. | |
| 2003/0055417 A1 | 3/2003 | Truckai et al. | |
| 2003/0158548 A1 | 8/2003 | Phan et al. | |
| 2003/0216732 A1 | 11/2003 | Truckai et al. | |
| 2004/0073256 A1 | 4/2004 | Marchitto et al. | |
| 2004/0176752 A1 | 9/2004 | Alfano et al. | |
| 2004/0260281 A1 | 12/2004 | Baxter, III et al. | |
| 2005/0033278 A1 | 2/2005 | McClurken et al. | |
| 2005/0059934 A1 | 3/2005 | Wenchell et al. | |
| 2005/0131390 A1 | 6/2005 | Heinrich et al. | |
| 2005/0234437 A1 | 10/2005 | Baxter et al. | |
| 2005/0261568 A1 | 11/2005 | Hular et al. | |
| 2006/0004406 A1* | 1/2006 | Wehrstein | A61B 17/28 606/205 |
| 2006/0089556 A1 | 4/2006 | Bambot et al. | |
| 2007/0179484 A1 | 8/2007 | Sade | |
| 2007/0225695 A1 | 9/2007 | Mayer et al. | |
| 2007/0299439 A1* | 12/2007 | Latterell | A61B 18/1445 606/48 |
| 2008/0046122 A1 | 2/2008 | Manzo et al. | |
| 2008/0077200 A1 | 3/2008 | Bendett et al. | |
| 2008/0221409 A1 | 9/2008 | Hoarau | |
| 2008/0247594 A1 | 10/2008 | Leclear et al. | |
| 2008/0319442 A1 | 12/2008 | Unger et al. | |
| 2009/0248007 A1 | 10/2009 | Falkenstein et al. | |
| 2009/0287194 A1 | 11/2009 | Gertz et al. | |
| 2009/0318912 A1 | 12/2009 | Mayer et al. | |
| 2010/0049187 A1 | 2/2010 | Carlton et al. | |
| 2010/0063500 A1 | 3/2010 | Muszala | |
| 2010/0076432 A1* | 3/2010 | Horner | A61B 18/1442 606/52 |
| 2010/0094271 A1 | 4/2010 | Ward et al. | |
| 2010/0100122 A1 | 4/2010 | Hinton | |
| 2010/0130971 A1 | 5/2010 | Baily | |
| 2010/0160904 A1 | 6/2010 | McMillan et al. | |
| 2010/0217258 A1 | 8/2010 | Floume et al. | |
| 2010/0228249 A1 | 9/2010 | Mohr et al. | |
| 2011/0224485 A1 | 9/2011 | Boulnois et al. | |
| 2011/0251605 A1 | 10/2011 | Hoarau et al. | |
| 2013/0185922 A1 | 7/2013 | Twomey | |
| 2013/0190753 A1 | 7/2013 | Garrison | |
| 2013/0190755 A1 | 7/2013 | Deborski | |
| 2013/0190760 A1 | 7/2013 | Allen, IV | |
| 2013/0197503 A1 | 8/2013 | Orszulak | |
| 2013/0218198 A1 | 8/2013 | Larson | |
| 2013/0218199 A1 | 8/2013 | Kerr | |
| 2013/0219691 A1 | 8/2013 | Reschke | |
| 2013/0226177 A1 | 8/2013 | Brandt | |
| 2013/0226178 A1 | 8/2013 | Brandt | |
| 2013/0226226 A1 | 8/2013 | Garrison | |
| 2013/0231662 A1 | 9/2013 | Kappus | |
| 2013/0232753 A1 | 9/2013 | Ackley | |
| 2013/0238016 A1 | 9/2013 | Garrison | |
| 2013/0238017 A1 | 9/2013 | Kerr | |
| 2014/0121508 A1 | 5/2014 | Latimer et al. | |
| 2014/0288541 A1 | 9/2014 | Eshkol et al. | |

FOREIGN PATENT DOCUMENTS

| | | |
|---|---|---|
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1 707 143 | 10/2006 |
| EP | 1 886 637 | 2/2008 |
| EP | 2 428 177 | 3/2012 |
| EP | 2 604 210 | 6/2013 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.

(56) References Cited

OTHER PUBLICATIONS

U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/873,780, filed Apr. 30, 2013, Kerr.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" Miccai 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report dated Oct. 22, 2013 in European Application No. 13 17 5304.

\* cited by examiner

OPTICAL SEALING DEVICE WITH CUTTING ABILITY

CROSS REFERENCE TO RELATED APPLICATION

The present application claims the benefit of and priority to U.S. Provisional Application Ser. No. 61/672,350, filed on Jul. 17, 2012, the entire contents of which are incorporated herein by reference.

BACKGROUND

Technical Field

The present disclosure relates to surgical instruments and, more particularly, to surgical forceps for grasping, treating, and/or dividing tissue.

Description of Related Art

A forceps is a plier-like instrument which relies on mechanical action between its jaws to grasp, clamp and constrict vessels or tissue. Energy-based forceps utilize both mechanical clamping action and energy, e.g., radiofrequency ("RF") energy, ultrasonic energy, microwave energy, thermal energy, light energy, etc., to affect hemostasis by heating tissue and blood vessels to coagulate and/or cauterize tissue. Certain surgical procedures require more than simply cauterizing tissue and rely on the unique combination of clamping pressure, precise energy control and/or gap distance (i.e., distance between opposing jaw members when closed about tissue) to "seal" tissue, vessels, and certain vascular bundles.

Typically, once a vessel is sealed, the surgeon has to accurately sever the vessel along the newly formed tissue seal. Accordingly, many forceps have been designed which incorporate a knife or blade member that effectively severs the tissue along the tissue seal. Alternatively, or additionally, energy may be utilized to facilitate tissue division.

SUMMARY

As used herein, the term "distal" refers to that portion that is further from an operator while the term "proximal" refers to that portion that is closer to an operator. As used herein, the term "treat" refers to performing a surgical treatment to tissue using energy, e.g. heating, sealing, or energized cutting of tissue. As used herein, the term "energy" refers broadly to include all types of energy used to treat tissue, e.g., RF energy, ultrasonic energy, microwave energy, thermal energy, light energy, etc. As used herein, the term "light energy source" refers broadly to include all types of devices that produce light for medical use (e.g., tissue treatment). These devices include lasers, light emitting diodes (LEDs), lamps, and other accessories that produce light anywhere along an appropriate electromagnetic spectrum (e.g., from infrared to ultraviolet).

Any or all of the aspects described herein, to the extent they are consistent, may be used in conjunction with any of the other aspects described herein.

In accordance with an aspect of the present disclosure, there is provided a forceps including an end effector assembly, a handle assembly, a first switch assembly, and a second switch assembly. The end effector includes first and second jaw members. One or both of the jaw members is movable relative to the other between a spaced-apart position, a first approximated position wherein the jaw members define a first gap distance "G" therebetween, and a second approximated position wherein the jaw members define a second gap distance "g" therebetween. One or both of the jaw members is adapted to connect to a source of energy. The handle assembly includes a movable handle operably coupled to the end effector, and is movable between an initial stage, a first actuated stage, and a second actuated stage for moving the jaw members between the spaced-apart position, the first approximated position, and the second approximated position. The first switch assembly is selectively activatable to supply a first energy to the jaw member(s) to seal tissue grasped between the jaw members when the jaw members are disposed in the first approximated position. The second switch assembly is selectively activatable to supply a second energy to the jaw member(s) to cut tissue grasped between the jaw members.

In an aspect, the second switch assembly may be operably positioned relative to the movable handle such that the second switch assembly is activated upon movement of the movable handle to the second actuated stage.

In an aspect, one or both of the jaw members include at least one tissue contacting member adapted to connect to the source of energy for treatment of the tissue that is grasped between the jaw members.

In an aspect, one or both of the jaw members may include tissue contacting members which include a plurality of elements, e.g. a first element configured to transmit the first energy to seal tissue grasped between the jaw members, and a second element configured to transmit the second energy to cut tissue grasped between the jaw members.

In aspects of the disclosure, the first switch assembly may be automatically activated upon movement of the movable handle to the first actuated stage. The first and/or second energy may be light energy having the same or different intensities and wavelengths. Further, the first and second pressures applied to the jaw members may be directly proportional to the intensity, wavelength or both, or the pressure may be inversely proportional, depending on the shape of the jaw member or other factors.

In accordance with another aspect of the present disclosure, there is provided a forceps including an end effector assembly, a handle assembly cooperable with a trigger assembly, a first switch assembly, and a second switch assembly. The end effector assembly includes first and second jaw members. One or both of the jaw members is movable relative to the other between a spaced-apart position, a first approximated position wherein the jaw members define a first gap distance "G" therebetween, and a second approximated position wherein the jaw members define a second gap distance "g" therebetween. One or both of the jaw members is adapted to connect to a source of energy. The handle assembly is operably coupled to the end effector assembly and is transitionable between an initial stage, a first actuated stage and a second actuated stage for moving the jaw members between the spaced-apart position, the first approximated position, and the second approximated position. The handle assembly includes a movable handle movable between an initial position and a compressed position to transition the handle assembly between the initial stage and the first actuated stage. The trigger assembly is movable between an un-actuated position and an actuated position to transition the handle assembly between the first actuated stage and the second actuated stage. The first switch assembly is selectively activatable to supply a first energy to the jaw member(s) to seal tissue grasped between the jaw members when the jaw members are disposed in the first approximated position. The second switch assembly is selectively activatable to supply a second energy to the jaw member(s) to cut tissue grasped between the jaw members.

In an aspect, the second switch assembly may be operably positioned relative to the movable handle such that the second switch assembly is activated upon movement of the movable handle to the second actuated stage.

In an aspect, one or both of the jaw members include at least one tissue contacting member adapted to connect to the source of energy for treatment of the tissue that is grasped between the jaw members.

In an aspect, one or both of the jaw members may include tissue contacting members which include a plurality of elements, e.g., a first element configured to transmit the first energy to seal tissue grasped between the jaw members, and a second element configured to transmit the second energy to cut tissue grasped between the jaw members.

In aspects of the disclosure, the first switch assembly may be automatically activated upon movement of the movable handle to the first actuated stage. The first and/or second energy may be light energy having the same or different intensities and wavelengths. Further, the first and second pressures applied to the jaw members may be directly proportional to the intensity, wavelength or both, or the pressure may be inversely proportional, depending on the shape of the jaw member or other factors.

Another aspect of the present disclosure provides a method of treating tissue. The method includes providing a forceps including an end effector assembly having first and second jaw members, one or both of the jaw members adapted to connect to a source of energy; moving the jaw members from a spaced-apart position to a first approximated position to grasp tissue therebetween under a first pressure; activating a first switch to supply a first energy to the jaw member(s) to seal tissue grasped between the jaw members; moving the jaw members from the first approximated position to a second approximated position to grasp tissue therebetween under a second, increased pressure; and activating a second switch to cut tissue grasped between the jaw members.

In an aspect, the second switch is automatically activated to supply a second energy to at least one jaw member upon movement of the jaw members to the second approximated position.

In aspects of the disclosure, the first and/or second energy may be light energy having the same or different intensities and wavelengths. Further, the first and second pressures applied to the jaw members may be directly proportional to the intensity, wavelength or both, or the pressure may be inversely proportional, depending on the shape of the jaw member or other factors.

BRIEF DESCRIPTION OF THE DRAWINGS

Various aspects of the present disclosure are described herein with reference to the drawings wherein like reference numerals identify similar or identical elements.

DETAILED DESCRIPTION

The present disclosure relates generally to apparatus, systems and methods for treating tissue, e.g., heating, sealing and/or dividing tissue using energy. The present disclosure is particularly advantageous for treating tissue using light energy, although the present disclosure is equally applicable for use with various other forms of energy, e.g., RF energy, ultrasonic energy, microwave energy, thermal energy, etc. However, while different considerations may apply depending on the particular form of energy used, the novel aspects of the present disclosure remain generally consistent regardless of the form of energy used. For simplicity and consistency purposes, the various aspects of the present disclosure will be described hereinbelow with respect to treating tissue using light energy.

Figure 1A:
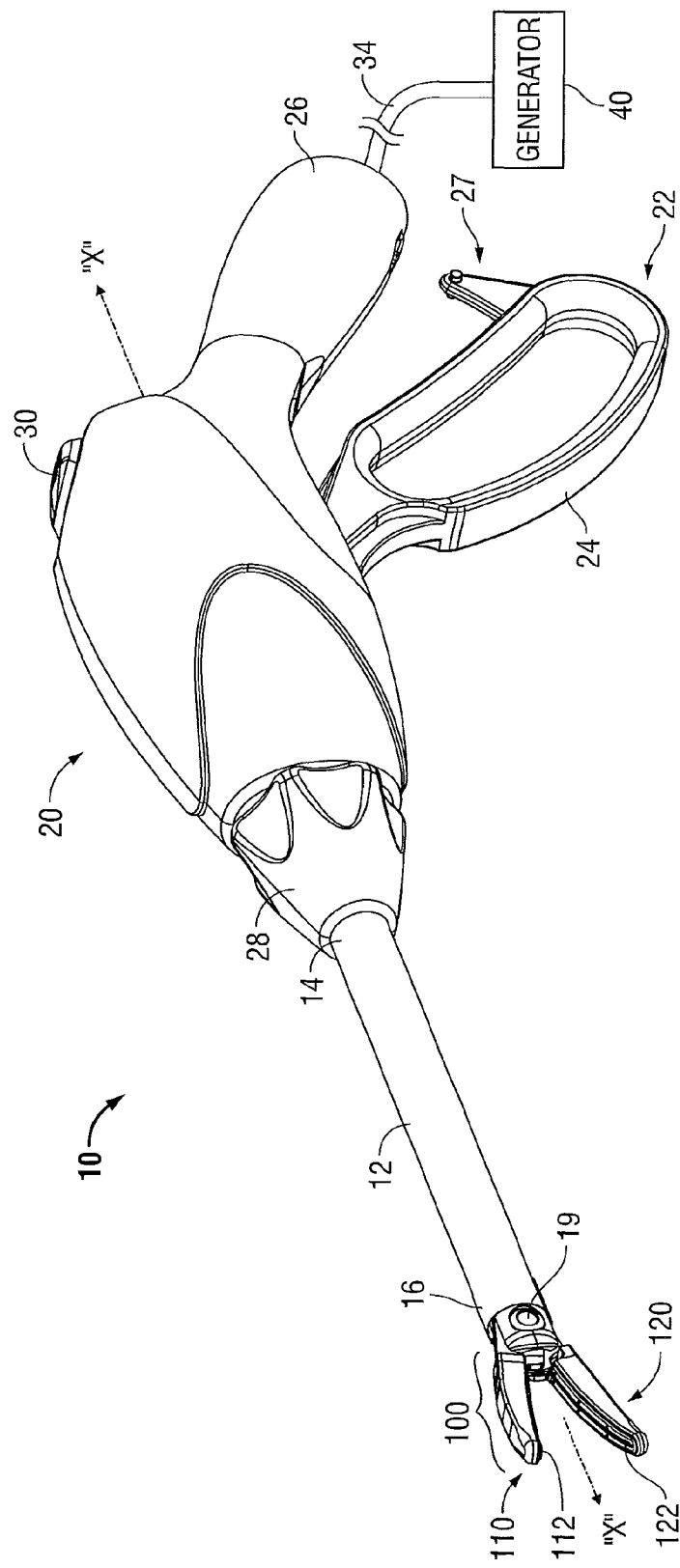
FIG. 1A is a perspective view of an endoscopic forceps provided in accordance with the present disclosure.
Figure 2A:
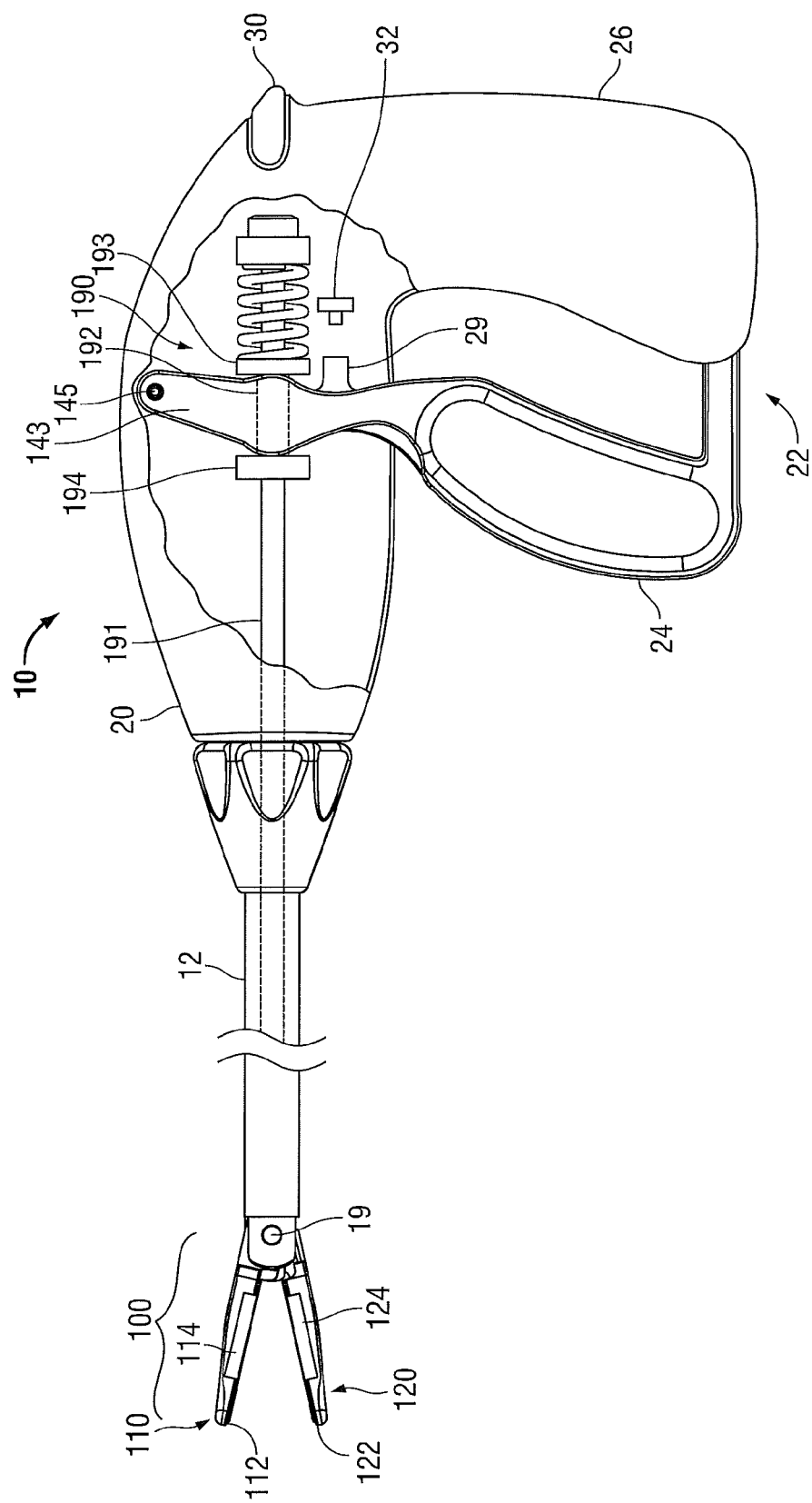
FIG. 2A is a side, cut-away view of another endoscopic forceps in accordance with the present disclosure, wherein the handle assembly is disposed in an initial open stage.

Turning now to FIG. 1A, forceps 10 defines a longitudinal axis "X-X" and includes a shaft 12, a housing 20, a handle assembly 22, a rotating assembly 28, an end effector assembly 100, a first switch assembly 30, a second switch assembly 32 (FIG. 2A), and a drive assembly 190 (FIG. 2A). Handle assembly 22 of forceps 10 includes a movable handle 24, a latching mechanism 27, and a fixed handle 26. Fixed handle 26 is integrally associated with housing 20 and movable handle 24 is movable relative to fixed handle 26. Movable handle 24 is ultimately connected to drive assembly 190 (FIG. 2A) that, together, mechanically cooperate to impart movement of jaw members 110, 120 of end effector assembly 100 between a spaced-apart position (P0) and a first approximated position (P1) to grasp tissue therebetween under a first pressure, and a second approximated position (P2) to grasp tissue therebetween under a second, greater pressure.

Shaft 12 has a distal end 16 configured to mechanically engage end effector assembly 100 and a proximal end 14 that mechanically engages housing 20. A cable 34 couples forceps 10 to an energy source, e.g., generator 40, for transmitting light energy (or other forms of energy), power, and/or control signals between the energy source and forceps 10. Generator 40 generates light energy adapted to treat tissue. In particular, generator 40 may be configured to output laser light energy having a wavelength from about 200 nm to about 11,000 nm. Alternatively or additionally, generator 40 may be configured to produce various other forms of energy, e.g., RF energy, ultrasonic energy, etc., for treating tissue, providing power to forceps 10, and/or other functions. Cable 34 is internally divided within handle assembly 22 and shaft 12 to transmit light energy and/or other forms of energy through various paths and ultimately to end effector assembly 100. Although generator 40 is shown to be external to forceps 10, generator 40 may alternatively located within forceps 10, and alternatively or additionally, forceps 10 may be battery powered.

End effector assembly 100, as mentioned above, is attached at distal end 16 of shaft 12 and includes a pair of opposing jaw members 110 and 120. Each jaw member 110, 120 includes a tissue contacting surface 112, 122, respectively. Tissue contacting surfaces 112, 122 cooperate to grasp and treat tissue held therebetween. Tissue contacting surfaces 112, 122 are ultimately connected to generator 40 (or any other suitable energy source) for transmitting energy, e.g., light energy, to tissue grasped therebetween.

One or both of the jaw members, e.g., jaw member 110, includes at least one tissue contacting member 114 disposed on or along tissue contacting surface 112 that is configured to facilitate the transmission of light energy from the light energy source, e.g., generator 40 (FIGS. 1A-1B) or internal energy source for battery powered embodiments, to tissue grasped between jaw members 110, 120. The other jaw member, e.g., jaw member 120, includes a tissue contacting surface 122 (or tissue contacting member 124 similar to tissue contacting member 114) that is configured to receive, absorb, or reflect the light energy transmitted from jaw member 110 and through tissue. Alternatively, energy may be transmitted from jaw member 120 to jaw member 110, or in both directions. Additionally, either or both tissue contacting member 114, 124 may include a plurality of elements each capable of producing a different energy than that of another element. For example, one element of tissue contacting member 114, 124 may be configured to transmit a first energy and another element of tissue contacting member 114, 124 may be configured to transmit a second energy.

End effector assembly 100 is designed as a bilateral assembly, e.g., wherein both jaw member 110 and jaw member 120 are movable about a pivot 19 relative to one another to grasp tissue. However, end effector assembly 100 may alternatively be configured as a unilateral assembly, e.g., where one of the jaw members, e.g., jaw member 120, is fixed relative to shaft 12 and the other jaw member, e.g., jaw member 110, is movable about pivot 19 relative to fixed jaw member 110, 120.

With continued reference to FIG. 1A, movable handle 24 is initially spaced-apart from fixed handle 26, wherein movable handle 24 is disposed in an initial stage (S0) and, accordingly, drive assembly 190 is disposed in a first position (see FIG. 2A). This initial stage (S0) corresponds to a spaced-apart position (P0) of jaw members 110, 120. As will be described below, movable handle 24 of forceps 10 is movable from this initial stage (S0), wherein drive assembly (FIGS. 2A-2C) is disposed in the first position (FIG. 2A), to one or more actuated stages, e.g., a first actuated stage (S1) and a second actuated stage (S2), to move drive assembly to a second position (see FIG. 2B), a third position (see FIG. 2C), etc., corresponding to one or more approximated positions of jaw members 110, 120, e.g., a first approximated position (P1) and a second approximated position (P2).

Latching mechanism 27 may be provided for selectively locking movable handle 24 relative to fixed handle 26 at various stages between the initial stage (S0) and the actuated stage(s) (S1, S2) to lock jaw members 110, 120 at various different positions during pivoting, e.g., to lock jaw members 110, 120 in the one or more approximated positions. Rotating assembly 28 is rotatable in either direction about longitudinal axis "X-X" to rotate end effector 100 about longitudinal axis "X-X."

Continuing with reference to FIG. 1A, a first switch assembly 30 disposed on housing 20 is selectively activatable to provide light energy from generator 40 (or any other suitable energy source) to tissue contacting surface 112 of jaw member 110 (and/or tissue contacting surface 122 of jaw member 120) of end effector assembly 100. More particularly, first switch assembly 30 may be configured to supply light energy to end effector assembly 100 for a first mode of operation, e.g., tissue sealing. First switch assembly 30 may be manually activated or may be automatically activated.

A second switch assembly 32 (see FIGS. 2A-2C) is disposed within housing 20 and is configured to supply light energy (or a different form of energy) to end effector assembly 100 for a second mode of operation, e.g., tissue cutting. Second switch assembly 32 is automatically activated upon achieving the second actuated stage (S2), as will be described in greater detail below. Although two switch assemblies 30, 32 are shown, forceps 10 may alternatively include greater or fewer than two switch assemblies 30, 32 for performing various tissue treatment procedures and/or for operating end effector assembly 100 in various modes. For example, forceps 10 may include a progressive switch (not shown) configured to apply more energy, a different type of energy or a different form of energy to end effector assembly 100 as handle assembly 22 is actuated.

Figure 1B:
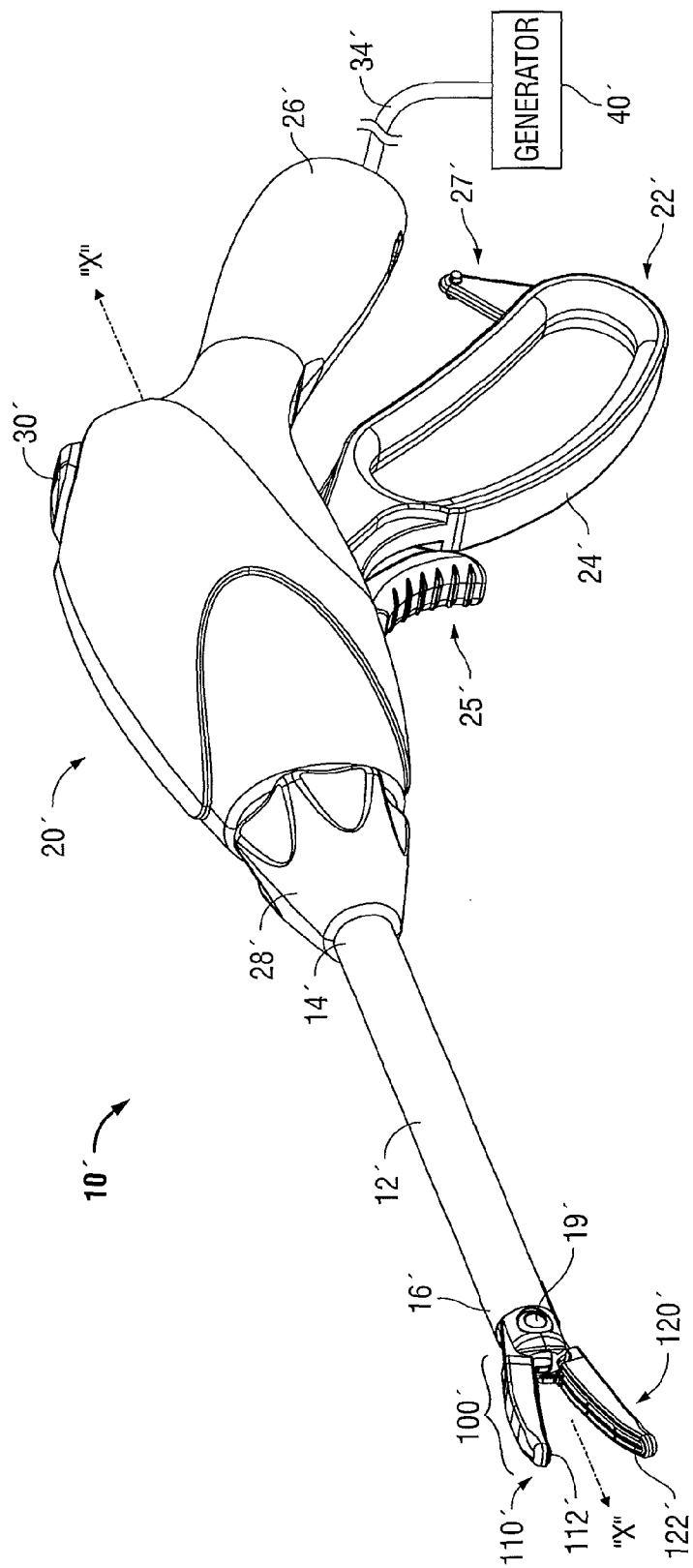
FIG. 1B is a perspective view of another endoscopic forceps provided in accordance with the present disclosure having a trigger assembly.
Figure 3A:
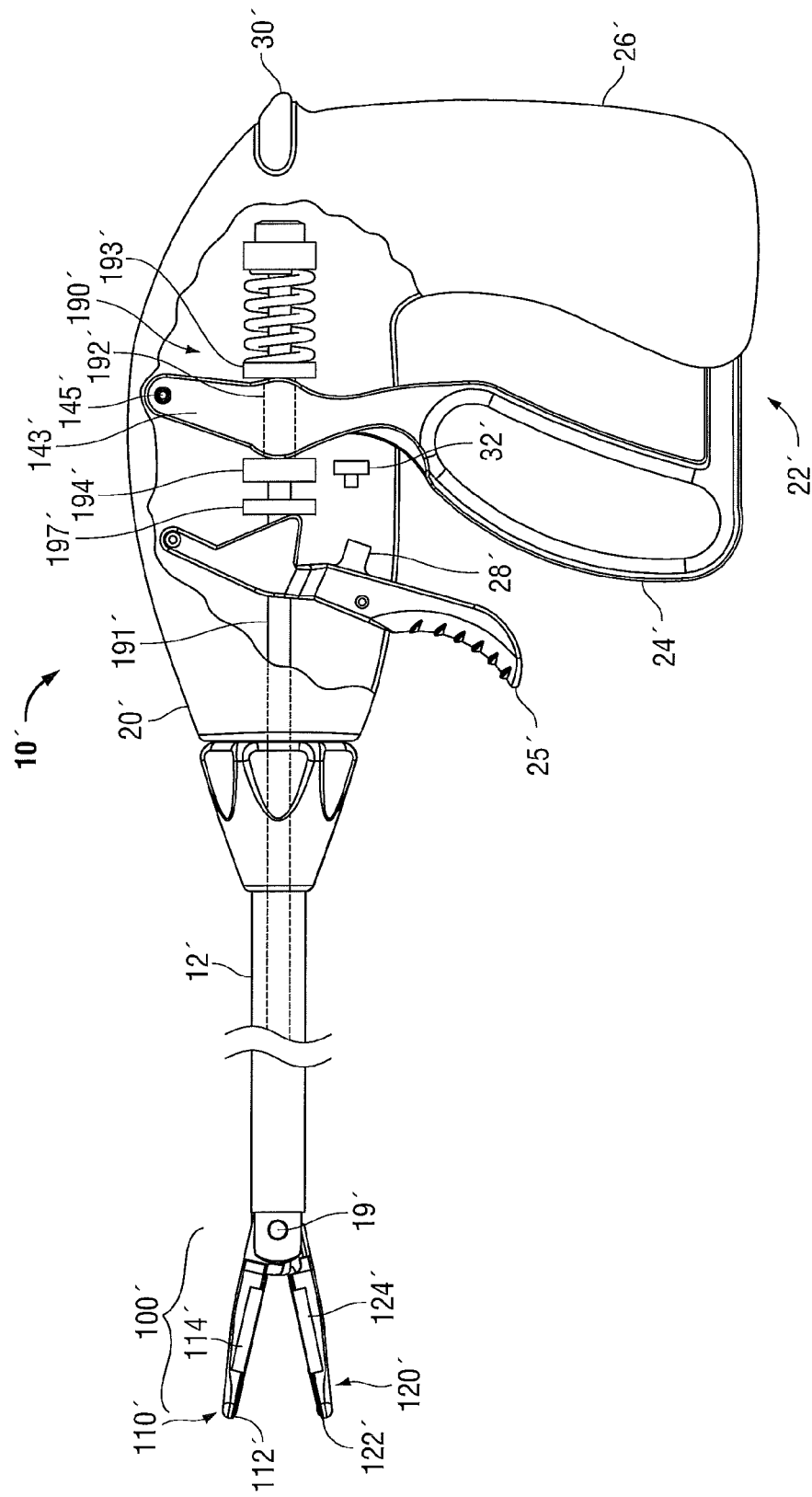
FIG. 3A is a side, cut-away view of another endoscopic forceps in accordance with the present disclosure, wherein the handle assembly is disposed in an initial open stage.

Turning now to FIG. 1B, another embodiment of a forceps 10' configured for use with end effector assembly 100' is shown. Forceps 10' defines a longitudinal axis "X-X" and includes a shaft 12', a housing 20', a handle assembly 22', a rotating assembly 28', an end effector assembly 100', a first switch assembly 30', a second switch assembly 32' (FIG. 3A), and a drive assembly 190' (FIG. 3A). Handle assembly 22' of forceps 10' includes a movable handle 24', a latching mechanism 27', a fixed handle 26', and a trigger assembly 25'. Fixed handle 26' is integrally associated with housing 20' and movable handle 24' is movable relative to fixed handle 26'. Movable handle 24' is ultimately connected to drive assembly 190' (FIG. 3A) which, together, mechanically cooperate to impart movement of jaw members 110', 120' of end effector assembly 100' between a spaced-apart position (P0) and a first approximated position (P1) to grasp tissue therebetween under a first pressure. Trigger assembly 25' and drive assembly 190' (FIG. 3A) are also mechanically cooperable to impart movement of jaw members 110', 120' of end effector assembly 100' between the first approximated position (P1) and the second approximated position (P2), wherein jaw members 110', 120' grasp tissue therebetween under a second, increased pressure. Forceps 10', except where specifically distinguished, is otherwise similar to and may include any of the features of forceps 10 (FIG. 1A). Accordingly, those features will only be summarized, or omitted entirely from the description of forceps 10' to avoid unnecessary repetition.

With continued reference to FIG. 1B, movable handle 24' is initially spaced-apart from fixed handle 26', wherein movable handle 24' is disposed in an initial stage (S0) and, accordingly, drive assembly 190' is disposed in an first position (see FIG. 3A). This initial stage (S0) corresponds to an initial spaced-apart position (P0) of jaw members 110', 120'. As will be described below, movable handle 24' of forceps 10' is movable from the initial stage (S0), wherein drive assembly 190' is disposed in the first position (FIG. 3A), to a first actuated stage (S1) to move drive assembly 190' from the first position (see FIG. 3A) to the second position (see FIG. 3B), thereby moving jaw members 110', 120' from the spaced-apart position (P0) to the first approximated position (P1), while trigger assembly 25' of forceps 10' is selectively actuatable to achieve the second actuated stage (S2), e.g., to move drive assembly 190' from the second position (see FIG. 3B) to a third position (see FIG. 3C), to thereby move jaw members 110', 120' to the second approximated position (P2).

Continuing with reference to FIG. 1B, forceps 10' further includes first and second switch assemblies 30', 32' (see FIG. 3A), although greater or fewer switch assemblies may also be provided. First switch assembly 30' is configured to supply light energy to end effector assembly 100' for a first mode of operation, e.g., tissue sealing, while second switch assembly 32' (see FIGS. 3A-3C) is disposed within housing 20' and is configured to supply light energy (or a different form of energy) to end effector assembly 100' for a second mode of operation, e.g., tissue cutting. Second switch assembly 32' is automatically activated upon achieving the second actuated stage (S2).

Light energy is suitable for sealing tissue since it is converted into heat energy by absorption at a molecular level. That is, light energy at optical wavelengths (e.g., from about 200 nm to about 11,000 nm) is used to heat tissue due to absorption of light energy at these wavelengths. However, optical properties of tissue are known to change during heating. For example, properties such as the absorption coefficient ($\mu_a$), scattering coefficient ($\mu_s$), and anisotropy coefficient (g) have been shown to change as a function of temperature and time. These properties, in turn, affect the transmission and reflection of light as it interacts with tissue.

It has been found that, due to the above, varying the pressure and energy applied to tissue during the application of light energy to tissue facilitates the formation of a tissue seal and, subsequently, the division of tissue along the tissue seal. More specifically, it has been found that initially applying a relatively smaller pressure and a first energy to tissue allows for creation of an effective tissue seal and that, once the tissue seal has been effectively formed, increasing the pressure and applying a second energy (e.g., light energy or another type of energy) facilitates the cutting of tissue. Forceps 10, 10' (FIGS. 1A and 1B, respectively), implement these advantageous findings by providing features that are configured to vary both the pressure and energy exerted on tissue grasped between jaw members 110, 120 (and 110', 120') thereof during the application of light energy to tissue in order to facilitate sealing and/or cutting of tissue.

Figure 2B:
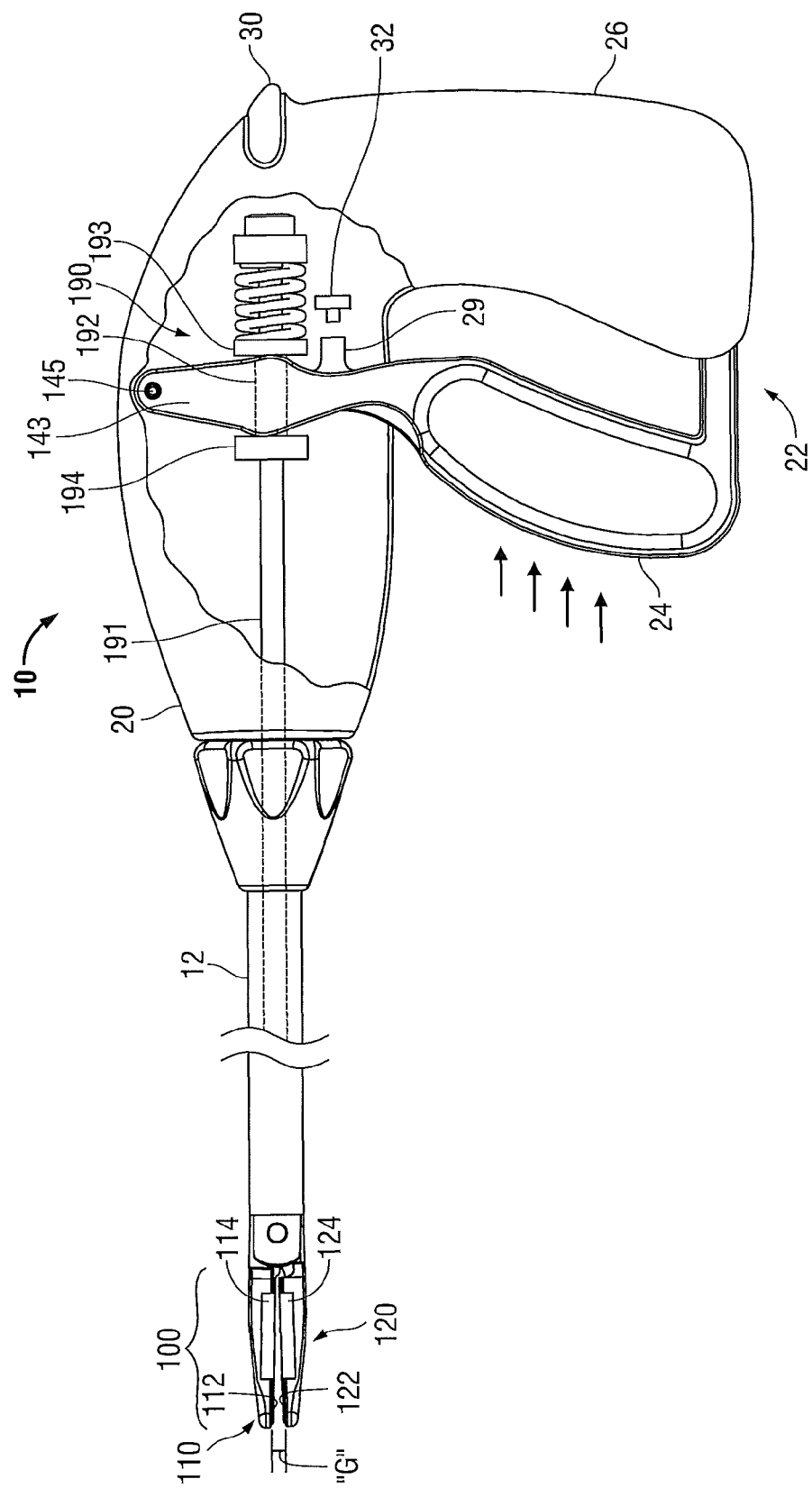
FIG. 2B is a side, cut-away view of the forceps of FIG. 2A, wherein the handle assembly is disposed in a first actuated stage.
Figure 2C:
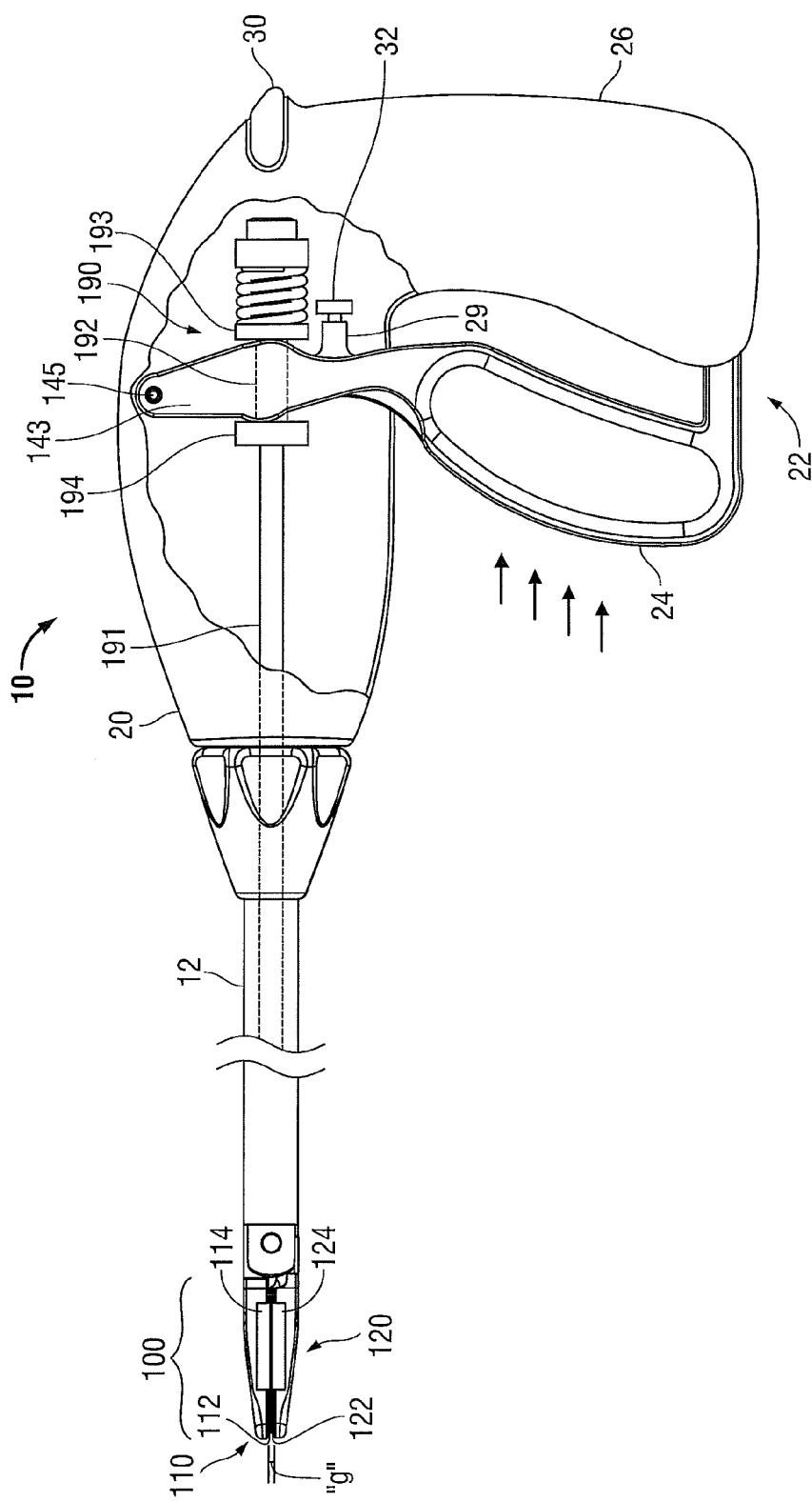
FIG. 2C is a side, cut-away view of the forceps of FIG. 2A, wherein the handle assembly is disposed in a second actuated stage.

Turning now to FIGS. 2A-2C, drive assembly 190 of forceps 10 includes a drive bar 191 that is disposed about longitudinal axis "X-X" and extends distally through housing 20 and shaft 12, ultimately coupling to jaw members 110, 120 of end effector assembly 100. More specifically, drive bar 191 is coupled to jaw members 110, 120, e.g., via pin-slot engagement (not explicitly shown), such that proximal translation of drive bar 191 pulls jaw members 110, 120 to rotate about pivot 19 relative one another, e.g., from the spaced-apart position (P0) (FIG. 2A) to the first approximated position (P1) (FIG. 2B). Distal translation of drive bar 191 pushes jaw members 110, 120 to rotate about pivot 19 away from one another, e.g., from the first approximated position (P1) (FIG. 2A) to the initial, spaced-apart position (P2) (FIG. 2B). The reverse configuration, e.g., wherein distal translation of drive bar 191 effects closure of jaw members 110, 120 and where proximal translation of drive bar 191 opens jaw members 110, 120, or any other suitable drive mechanism (not shown) may also be provided.

Drive assembly 190 further includes a mandrel 192 disposed about drive bar 191 toward a proximal end thereof. Mandrel 192 includes proximal and distal rims 193, 194, respectively. Mandrel 192 is fixedly engaged to drive bar 191 and is annularly disposed between drive bar 191 and flanges 143 of movable handle 24. Proximal and distal rims 193, 194, respectively, of mandrel 192 extend radially outwardly therefrom to retain flanges 143 of movable handle 24 therebetween. Accordingly, as movable handle 24 is moved proximally, e.g., as movable handle 24 is pivoted about pivot pin 145 from the initial stage (S0) to the first actuated stage (S1) to the second actuated stage (S2), flanges 143 contact proximal rim 193 of mandrel 192 and urge drive bar 191 proximally from the first position (FIG. 2A) to the second position (FIG. 2B), to the third position (FIG. 2C). On the other hand, as movable handle 24 is moved distally, e.g., as movable handle 24 is returned to the initial stage (S0), flanges 143 contact distal rim 194 of mandrel 192 and urge drive bar 191 distally, thereby returning drive bar 191 to the first position as movable handle 24 is returned to the initial stage (S0). Put more generally, mandrel 192 couples flanges 143 of movable handle 24 to drive bar 191 such that jaw members 110, 120 are moved between the spaced-apart position (P0) (FIG. 2A), the first approximated position (P1) (FIG. 2B), and the second approximated position (P2) (FIG. 2C) as movable handle 24 is moved between the initial stage (S0), the first actuated stage (S1), and the second actuated stage (S2).

With reference to FIG. 2A, forceps 10 is shown wherein movable handle 24 is disposed in the initial stage (S0) such that drive assembly 190 is disposed in the first position. Accordingly, jaw members 110, 120 are spaced-apart relative to each other in an initial, spaced-apart position (P0). At this point, jaw members 110, 120 may be placed over, around, or otherwise in contact with tissue to be grasped.

Referring now to FIG. 2B, when moveable handle 24 is moved from the initial stage (S0) to the first actuated stage (S1), drive bar 191 is translated proximally to move drive assembly 190 to the second position, thereby moving jaw members 110, 120 from the spaced-apart position (P0) to the first approximated position (P1) to grasp tissue therebetween or otherwise apply a first pressure to tissue therebtween. More specifically, with jaw members 110, 120 disposed in the first approximated position (P1), as shown in FIG. 2B, a first, relatively large gap distance "G" is defined between tissue contacting surfaces 112, 122 of jaw members 110, 120, respectively, and, as a result of this relatively larger gap distance "G" between jaw members 110, 120, a relatively smaller pressure is applied to tissue grasped therebetween.

Continuing with reference to FIG. 2B, with jaw members 110, 120 disposed in the first approximated position (P1) and grasping tissue between tissue contacting surfaces 112, 122, respectively, thereof, a first energy may be transmitted from tissue contacting member 114 of jaw member 110, through tissue, to tissue contacting member 124 of jaw member 120 (although energy may alternatively be transmitted between tissue contacting members 114, 124 in either or both directions) to seal tissue grasped between jaw members 110, 120. The first energy may be a particular intensity, radiance, flux, wavelength, etc. of light energy. Additionally, or alternatively, either (or both) tissue contacting members 114, 124 may include a plurality of different elements capable of applying different types of energy (differing in type of energy, wavelength, intensity, radiance, flux, etc.). In such a configuration, a particular number or combination of energy applying elements may be activated to supply the first energy.

Activation of the first energy may be effected by manually activating first switch assembly 30. Alternatively, the first energy may be effected automatically upon actuation of movable handle 24. As mentioned above, with jaw members 110, 120 disposed in the first approximated position (P1) defining first gap distance "G" therebetween, a relatively smaller pressure is applied to tissue. As such, upon activation of first switch assembly 30, or otherwise applying the first energy to tissue grasped between jaw members 110, 120, maximum absorption of light energy by tissue to facilitate the sealing of tissue grasped between jaw members 110, 120 can be achieved.

With reference to FIG. 2C, forceps 10 is shown wherein handle assembly 22 is disposed in the second actuated stage (S2). With jaw members 110, 120 disposed in the first approximated position (P1) and handle assembly 22 disposed in the first actuated stage (S1), movable handle 24 is squeezed further towards fixed handle 26 to thereby move drive bar 191 further proximally such that drive assembly 190 is moved to the third position, thereby pivoting jaw members 110, 120 relative to one another from the first approximated position (P1) to the second approximated position (P2), to further grasp tissue therebetween or otherwise apply a second pressure to tissue therebetween. The second pressure is greater than the first pressure exerted when jaw members are disposed in the first approximated position (P1). With jaw members 110, 120 disposed in the second approximated position (P2), as shown in FIG. 2C, a second gap distance "g" that is smaller than first gap distance "G" is defined between tissue contacting surfaces 112, 122 of jaw members 110, 120, respectively, and, as a result, the relatively larger pressure is applied to tissue grasped therebetween.

Continuing with reference to FIG. 2C, as jaw members 110, 120 are moved to the second approximated position (P2) and tissue is grasped between tissue contacting surfaces 112, 122, respectively, a second energy is applied, e.g., a second energy is transmitted from tissue contacting member 114 of jaw member 110, through tissue, to tissue contacting member 124 of jaw member 120, (although energy may alternatively be transmitted between tissue contacting members 114, 124 in either or both directions). The second energy may vary from the first energy in intensity, radiance, flux, wavelength, or other ways. Alternatively, or additionally, the second energy may be transmitted by a different tissue contacting member 114, 124 disposed on either or both of tissue contacting surfaces 112, 122, or a different element (or elements) of either of both tissue contacting member 114, 124. Additionally or alternatively, the first and/or second energy may be light energy having the same or different intensities and wavelengths. Additionally, the first and second pressures applied to the jaw members may be directly proportional to the intensity, wavelength or both. Alternatively, the pressure may be inversely proportional depending on the shape of the jaw member.

Activation of the second energy, as shown in FIG. 2C, is effected automatically upon movement of movable handle 24 to the second actuated stage (S2). More specifically, movable handle 24 includes a protrusion 29 extending proximally therefrom that is configured to activate second switch assembly 32 upon movement of movable handle 24 to the second actuated stage (S2). Other configurations for activating second switch assembly 32 upon movement of movable handle 24 to the second actuated stage (S2) are also contemplated. As mentioned above, with jaw members 110, 120 disposed in the second approximated position (P2) defining second gap distance "g" therebetween, a relatively greater pressure is applied to tissue and a second energy is applied to tissue to facilitate cutting of tissue along the previously formed tissue seal. Thus, handle assembly 22, drive assembly 190, first and second switch assemblies 30, 32, and jaw members 110, 120 cooperate to apply a first pressure and first energy to tissue to seal tissue and, subsequently, e.g., upon moving movable handle 24 to the second actuated stage (S2), to simultaneously and automatically apply a second pressure and second energy to tissue to cut tissue along the tissue seal. Typically, during tissue sealing, the closure pressure between jaw members 110, 120 is in the range of about 3 kg/cm² to about 16 kg/cm², although other closure pressure ranges are also contemplated. Typically, for tissue-sealing, the gap distance "G" between tissue contacting surfaces 112, 122 is in the range of about 0.001 inches to about 0.006 inches, although other gap distances are also contemplated.

Alternatively, jaw members 110, 120 may be moved to an intermediate approximated position for completion of the tissue seal, and may then be moved to the second approximated position for cutting tissue along the previously formed tissue seal. At the completion of tissue treatment, e.g., sealing and/or cutting of tissue, jaw members 110, 120 are returned to the spaced-apart position (P0) and end effector assembly 100 is removed from the surgical site (or is repositioned adjacent other tissue to be treated).

Handle assembly 22, as mentioned above, may also include a latching mechanism 27 for releasably retaining movable handle 26 in the first actuated stage (S1) and/or the second actuated stage (S2), thus allowing the user to lock jaw members 110, 120 in the first approximated position (P1) for sealing tissue, and, subsequently, in the second approximated position (P2), for cutting tissue. Alternatively, movable handle 26 may be continuously moved from the initial stage (S0), through the first actuated stage (S1), and ultimately, to the second actuated stage (S2) such that tissue is grasped under a first pressure and a first energy is applied to seal tissue and such that tissue is grasped under a second, increased pressure and a second, different energy is applied to cut tissue along the tissue seal in one continuous motion of movable handle 26.

Figure 3B:
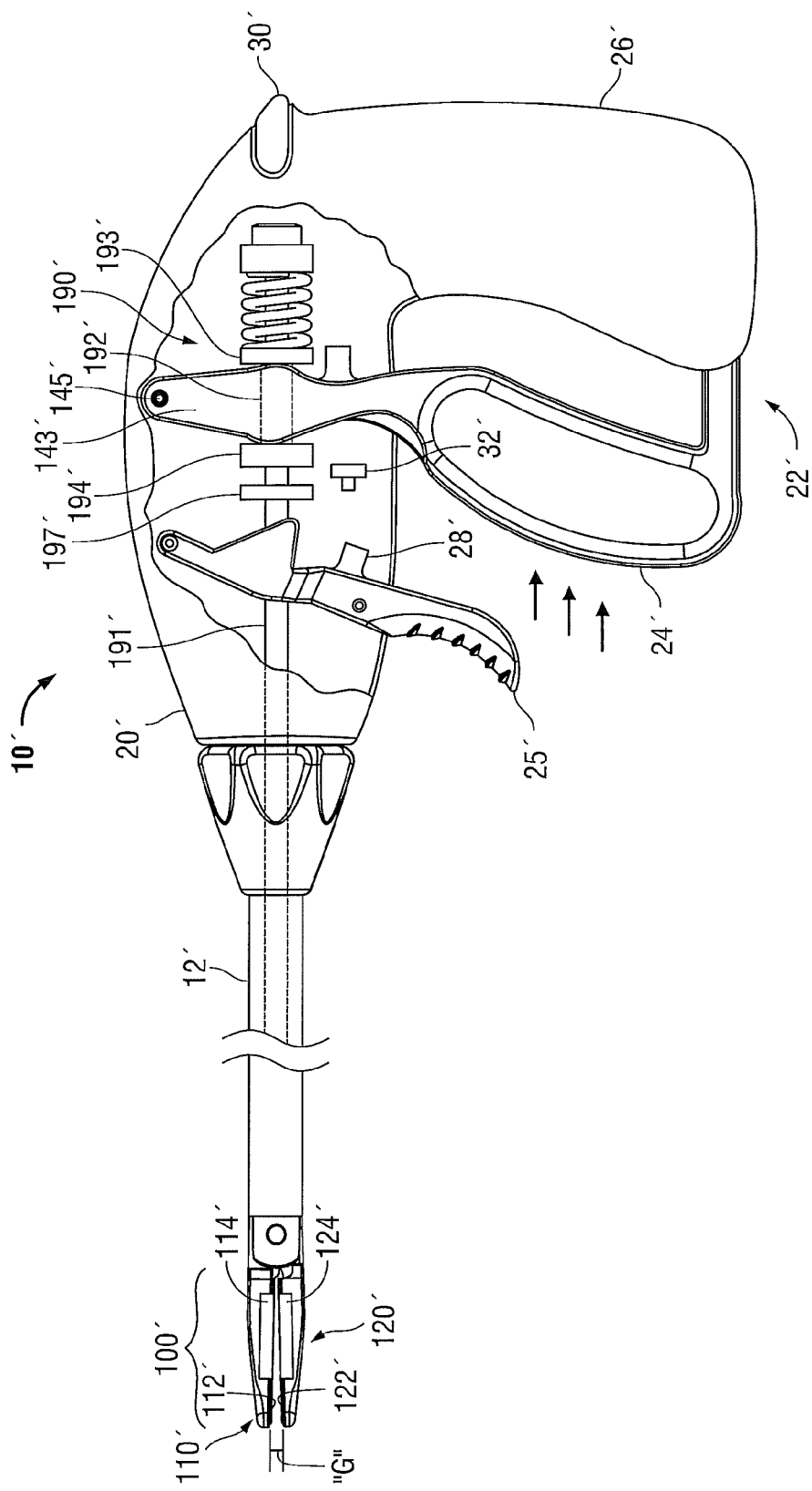
FIG. 3B is a side, cut-away view of the forceps of FIG. 3A, wherein the handle assembly is disposed in the first actuated stage.
Figure 3C:
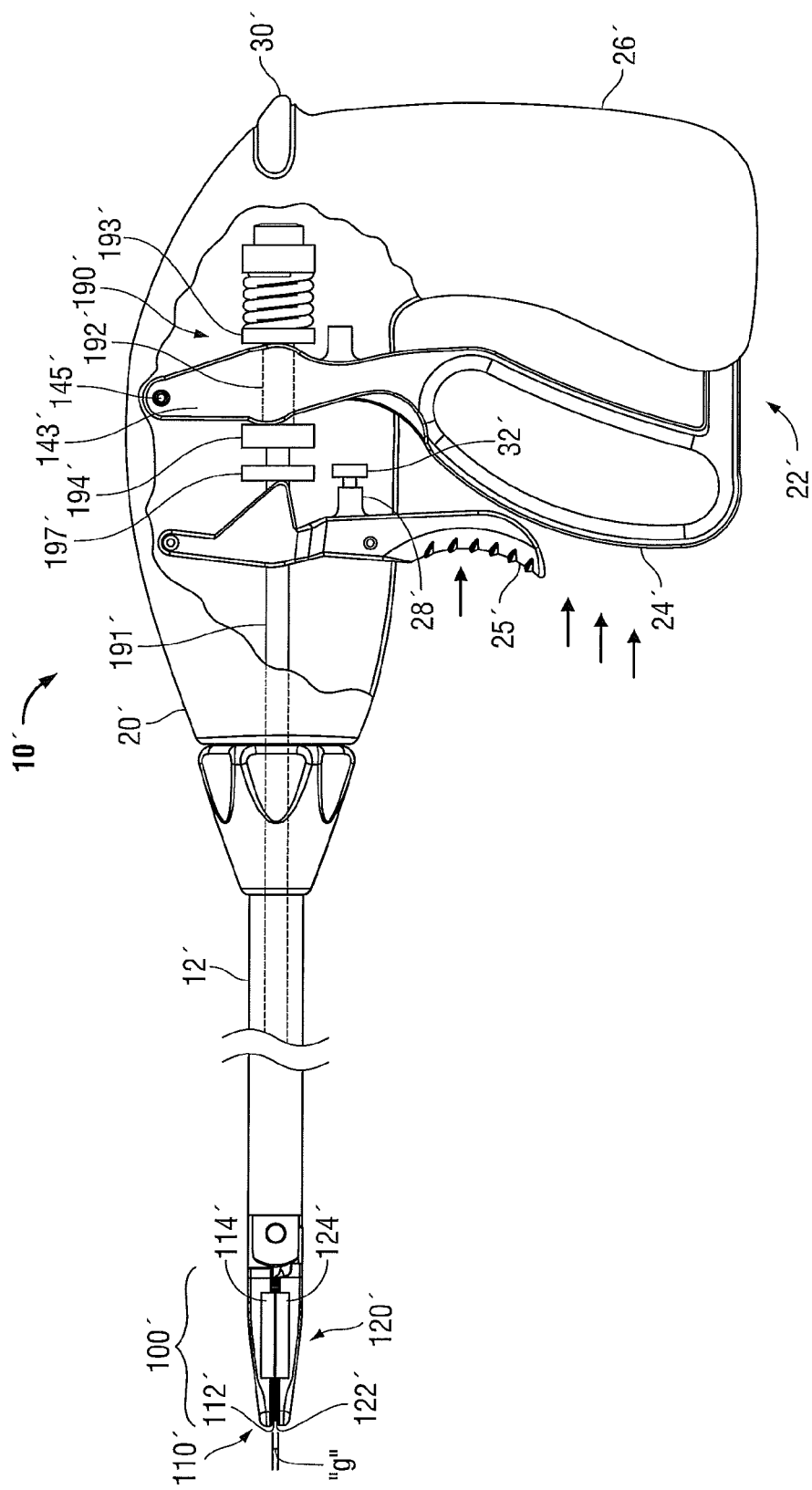
FIG. 3C is a side, cut-away view of the forceps of FIG. 3A, wherein the handle assembly is disposed in the second actuated stage.

Turning now to FIGS. 3A-3C, drive assembly 190' of forceps 10' operates similarly to drive assembly 190 of forceps 10. Mandrel 192' of drive assembly 190' is similar to mandrel 192 of drive assembly 190, but further includes trigger rim 197'. Additionally or alternatively, it is envisioned that multiple drive assemblies 190' may be included in forceps 10', each drive assembly 190' including a resilient member with a different resilient constant from that of a different drive assembly 190'.

Similar to drive assembly 190 of forceps 10, drive assembly 190' of forceps 10' operates in the same manner to urge drive bar 191' proximally from the first position (FIG. 3A) to the second position (FIG. 3B). However, urging drive assembly 190' from a second position (FIG. 3B) to a third position (FIG. 3C) is accomplished by actuation of trigger assembly 25' of forceps 10'. Drive assembly 190' of forceps 10' includes all the features of drive assembly 190 but further includes a trigger rim 197' disposed about drive bar 191' toward a proximal end thereof. Trigger rim 197' is fixedly engaged to drive bar 191' and is positioned in such a manner that actuation of trigger assembly 25' causes actuation of trigger rim 197' to further urge drive bar 191' from the second position (FIG. 3B) to the third position (FIG. 3C). Accordingly, as movable handle 24' is moved proximally, e.g., as movable handle 24' is pivoted about pivot pin 145' from the initial stage (S0) to the first actuated stage (S1), flanges 143' contact proximal rim 193' of mandrel 192' and urge drive bar 191' proximally from the first position (FIG. 3A) to the second position (FIG. 3B), and as trigger assembly 25' is moved proximally, trigger assembly 25' contacts trigger rim 197' and urges drive bar proximally from the second position (FIG. 3B.) to the third position (FIG. 3C), thereby achieving the second actuated stage (S2) of handle assembly 22'.

Turning now to FIG. 3A, forceps 10' is shown wherein movable handle 24' is disposed in the initial stage (S0) such that drive assembly 190' is disposed in the first position. Accordingly, jaw members 110', 120' of forceps 10' are spaced-apart relative to each other in an initial, spaced-apart position (P0). At this point, jaw members 110', 120' of forceps 10' may be placed over, around, or otherwise in contact with tissue to be grasped.

Referring now to FIG. 3B, when moveable handle 24' is moved from the initial stage (S0) to the first actuated stage (S1), drive bar 191' is translated proximally to move drive assembly 190' to the second position, thereby moving jaw members 110', 120' from the spaced-apart position (P0) to the first approximated position (P1) to grasp tissue therebetween or otherwise apply a first pressure to tissue therebetween. More specifically, with jaw members 110', 120' of forceps 10' disposed in the first approximated position (P1), as shown in FIG. 3B, a first, relatively large gap distance "G" is defined between tissue contacting surfaces 112', 122' of jaw members 110', 120' of forceps 10', respectively, and, as a result of this relatively larger gap distance "G" between jaw members 110', 120' of forceps 10', a relatively smaller pressure is applied to tissue grasped therebetween.

Continuing with reference to FIG. 3B, with jaw members 110', 120' of forceps 10' disposed in the first approximated position (P1) and grasping tissue between tissue contacting surfaces 112', 122', respectively, thereof, a first energy may be transmitted from tissue contacting member 114' of jaw member 110', through tissue, to tissue contacting member 124' of jaw member 120' (although energy may alternatively be transmitted between tissue contacting members 114', 124' in either or both directions) to seal tissue grasped between jaw members 110', 120'. The first energy may be a particular intensity, radiance, flux, wavelength, etc. of light energy. Additionally, or alternatively, either (or both) of tissue contacting members 114', 124' may include a plurality of different elements capable of applying different types of energy (differing in type of energy, wavelength, intensity, radiance, flux, etc.). In such a configuration, a particular number or combination of energy applying elements may be activated to supply the first energy.

Activation of the first energy may be effected by manually activating first switch assembly 30'. Alternatively or additionally, the first energy may be effected automatically upon actuation of movable handle 24' (similar to the activation of second switch assembly 32' described below). As mentioned above, with jaw members 110', 120' of forceps 10' disposed in the first approximated position (P1) defining first gap distance "G" therebetween, a relatively smaller pressure is applied to tissue. As such, upon activation of first switch assembly 30', or otherwise applying the first energy to tissue grasped between jaw members 110', 120', maximum absorption of light energy by tissue to facilitate the sealing of tissue grasped between the jaw members 110', 120' can be achieved.

With reference to FIG. 3C, forceps 10' is shown wherein handle assembly 22' is disposed in the second actuated stage (S2). With jaw members 110', 120' in a first approximated position (P1) and handle assembly 22' disposed in the first actuated stage (S1), trigger assembly 25' is squeezed towards fixed handle 26' to urge trigger rim 197' proximally, thereby urging drive bar 191' further proximally such that drive assembly 190' is moved to the third position, pivoting jaw members 110', 120' relative to one another from the first approximated position (P1) to the second approximated position (P2) to further grasp tissue therebetween or otherwise apply a second pressure to the tissue therebtween. The second pressure is greater than the first pressure exerted when jaw members 110', 120' are disposed in the first approximated position (P1). With jaw members 110', 120' disposed in the second approximated position (P2) as shown in FIG. 3C, a second gap distance "g" that is smaller than first gap distance "G" is defined between tissue contacting surfaces 112', 122' of jaw members 110', 120', respectively, and, as a result, the relatively larger pressure is applied to tissue grasped therebetween.

Continuing with reference to FIG. 3C, as jaw members 110, 120 are moved to the second approximated position (P2) to grasp tissue between tissue contacting surfaces 112', 122', respectively, thereof, a second energy is applied, e.g., a second energy is transmitted from tissue contacting member 114' of jaw member 110', through tissue, to tissue contacting member 124' of jaw member 120' (although energy may alternatively be transmitted between tissue contacting members 114', 124' in either or both directions). The second energy may vary from the first energy in intensity, radiance, flux, wavelength, or other ways. Alternatively, or additionally, the second energy may be transmitted by a different tissue contacting member 114', 124' disposed on either or both of tissue contacting surfaces 112', 122', or a different element (or elements) of either or both tissue contacting member 114', 124'. Additionally or alternatively, the first and/or second energy may be light energy having the same or different intensities and wavelengths. Additionally, the first and second pressures applied to the jaw members may be directly proportional to the intensity, wavelength or both. Alternatively, the pressure may be inversely proportional depending on the shape of the jaw member.

Activation of the second energy, as shown in FIG. 3C, is effected automatically upon movement of trigger assembly 25' to the second actuated stage (S2). More specifically, trigger assembly 25' includes a protrusion 28' extending proximally therefrom that is configured to activate second switch assembly 32' upon movement of trigger assembly 25' to the second actuated stage (S2). Other configurations for activating second switch assembly 32' upon movement of trigger assembly 25' to the second actuated stage (S2) are also contemplated. As mentioned above, with jaw members 110', 120' of forceps 10' disposed in the second approximated position (P2) defining second gap distance "g" therebetween, a relatively greater pressure is applied to tissue and a second energy is applied to tissue to facilitate cutting of tissue along the previously formed tissue seal. Thus, handle assembly 22', drive assembly 190', first and second switch assemblies 30', 32', and jaw members 110', 120' cooperate to apply a first pressure and first energy to tissue to seal tissue, and subsequently, e.g. upon moving trigger assembly 25' to the second actuated stage (S2), to simultaneously and automatically apply a second pressure and second energy to tissue to cut tissue along tissue seal. Typically, during tissue sealing, the closure pressure between jaw members 110', 120' is in the range of about 3 kg/cm$^2$ to about 16 kg/cm$^2$, although other closure pressure ranges are also contemplated. Typically, for tissue-sealing, the gap distance "G" between tissue contacting surfaces 112', 122' is in the range of about 0.001 inches to about 0.006 inches, although other gap distances are also contemplated.

Alternatively, jaw members 110', 120' of forceps 10' may be moved to an intermediate approximated position for completion of the tissue seal, and may then be moved to the second approximated position for cutting tissue along the previously formed tissue seal. At the completion of tissue treatment, e.g., sealing and/or cutting of tissue, jaw members

110', 120' of forceps 10' are returned to the spaced-apart position (P0) and end effector assembly 100' of forceps 10' is removed from the surgical site (or is repositioned adjacent other tissue to be treated).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly including first and second jaw members, at least one of the jaw members movable relative to the other between a spaced-apart position, a first approximated position wherein the jaw members define a first gap distance "G" therebetween configured to apply a first pressure to tissue clamped between the jaw members, and a second approximated position wherein the jaw members define a second gap distance "g" therebetween configured to apply a second pressure greater than the first pressure to tissue clamped between the jaw members, at least one of the jaw members adapted to connect to a source of energy;
   a handle assembly including a movable handle operably coupled to the end effector, the movable handle movable between an initial stage, a first actuated stage, and a second actuated stage for moving the jaw members between the spaced-apart position, the first approximated position, and the second approximated position;
   a first switch assembly selectively activatable to supply a first light energy to at least one jaw member to seal tissue grasped between the jaw members when the jaw members are disposed in the first approximated position; and
   a second switch assembly selectively activatable to supply a second light energy to the at least one jaw member to cut tissue grasped between the jaw members when the jaw members are disposed in the second approximated position, wherein each of the second pressure and the second light energy is individually insufficient to cut the tissue.

2. The forceps according to claim 1, wherein the second switch assembly is operably positioned relative to the movable handle, such that the second switch assembly is activated upon movement of the movable handle to the second actuated stage.

3. The forceps according to claim 1, wherein at least one of the first and second jaw members includes at least one tissue contacting member adapted to connect to the source of energy for treating tissue grasped between the jaw members.

4. The forceps according to claim 3, wherein the at least one tissue contacting member includes a plurality of elements, at least a first element configured to transmit the first light energy to seal tissue grasped between the jaw members and at least a second element configured to transmit the second light energy to cut tissue grasped between the jaw members.

5. The forceps according to claim 1, wherein the first switch assembly is automatically activated upon movement of the movable handle to the first actuated stage.

6. The forceps according to claim 1, wherein the handle assembly includes a latching mechanism configured to selectively latch the movable handle in the first actuated stage and the second actuated stage.

* * * * *